(12) United States Patent
Logan et al.

(10) Patent No.: US 9,377,384 B2
(45) Date of Patent: Jun. 28, 2016

(54) RAIL SHEAR TESTER APPARATUS WITH MULTIPLE LOADING CONFIGURATIONS

(71) Applicants: James D. Logan, Pullman, WA (US); Dean A. Nelson, Pullman, WA (US); Nathaniel D. Darnall, Pullman, WA (US); Timothy T. Meekhof, Moscow, ID (US); Peter A. Siebold, Pullman, WA (US); Ryan D. Baldwin, Cheney, WA (US); David E. Abbott, Viola, ID (US); Wayne P. Waldher, Clarkston, WA (US)

(72) Inventors: James D. Logan, Pullman, WA (US); Dean A. Nelson, Pullman, WA (US); Nathaniel D. Darnall, Pullman, WA (US); Timothy T. Meekhof, Moscow, ID (US); Peter A. Siebold, Pullman, WA (US); Ryan D. Baldwin, Cheney, WA (US); David E. Abbott, Viola, ID (US); Wayne P. Waldher, Clarkston, WA (US)

(73) Assignee: METRIGUARD INC, Pullman, WA (US)

( * ) Notice: Subject to any disclaimer, the term of this patent is extended or adjusted under 35 U.S.C. 154(b) by 0 days.

(21) Appl. No.: 14/693,035

(22) Filed: Apr. 22, 2015

(65) Prior Publication Data
US 2015/0316458 A1 Nov. 5, 2015

Related U.S. Application Data

(60) Provisional application No. 61/987,311, filed on May 1, 2014.

(51) Int. Cl.
*G01N 3/24* (2006.01)
*G01N 3/02* (2006.01)

(52) U.S. Cl.
CPC .. *G01N 3/02* (2013.01); *G01N 3/24* (2013.01); *G01N 2203/0282* (2013.01)

(58) Field of Classification Search
CPC .... G01N 2203/0282; G01N 3/24; G01N 3/02
USPC .................................................. 73/854–860
See application file for complete search history.

(56) References Cited

U.S. PATENT DOCUMENTS

| | | | | |
|---|---|---|---|---|
| 3,878,598 A * | 4/1975 | Steward | ................ | B23P 19/062 29/432.2 |
| 5,060,516 A * | 10/1991 | Lau | ...................... | G01M 5/0058 73/579 |
| 5,146,823 A * | 9/1992 | Holmes | ..................... | B26D 1/04 269/47 |
| 5,329,070 A * | 7/1994 | Knowles | ............... | G06F 3/0436 178/18.04 |
| 5,598,757 A * | 2/1997 | Lloyd | .................... | B23D 33/10 29/846 |
| 5,705,752 A * | 1/1998 | Chang | ...................... | G01N 3/24 73/827 |
| 2004/0069072 A1* | 4/2004 | Kawabe | .................. | G01N 3/24 73/841 |
| 2005/0178211 A1* | 8/2005 | Thom | ...................... | G01N 3/08 73/820 |

* cited by examiner

*Primary Examiner* — Max Noori

(57) ABSTRACT

An apparatus for testing panel products in edgewise shear in which the shear stress is applied in a diagonal direction with a first rotational degree of freedom in a first grip means and a second rotational degree of freedom in a second grip means as a first loading configuration. A second loading configuration is provided in which the second rotational degree of freedom of the second grip means is locked in place and motion is prevented. A third preferred method of loading is available in which shear forces in a horizontal direction through a centerline of a specimen, with the centerline in the plane of the specimen and extending across a widest dimension of said specimen. Control and data collection are under computer control and operator safety is enhanced by a locking guard door which is electrically locked while the various parts of the machine are in motion.

16 Claims, 17 Drawing Sheets

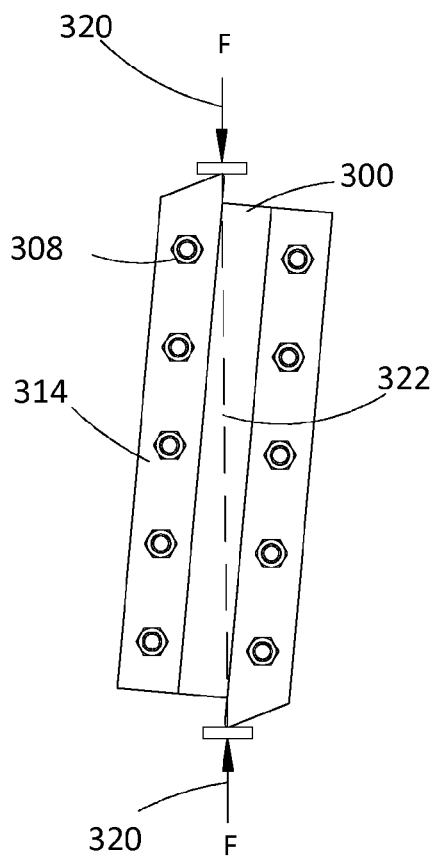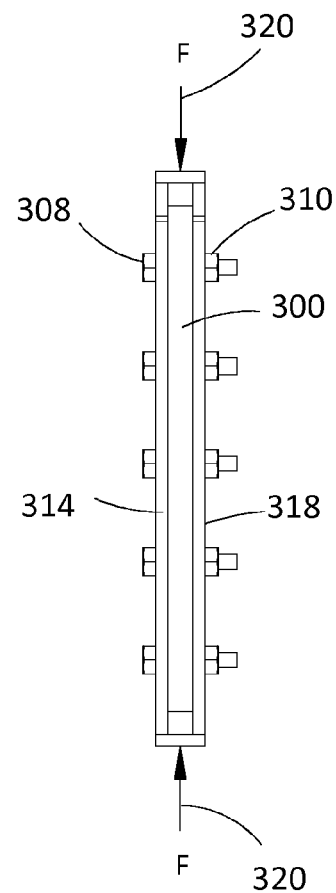
PRIOR ART
FIG 17
PRIOR ART
FIG 18

RAIL SHEAR TESTER APPARATUS WITH MULTIPLE LOADING CONFIGURATIONS

RELATED APPLICATION

Benefit is claimed of provisional application titled: "Rail Shear Tester Apparatus with multiple loading configurations" Application No. 61/987,311 filed 2014 May 1.

REGARDING FEDERALLY SPONSORED RESEARCH OR DEVELOPMENT

This invention was funded entirely by private funds in privately owned facilities. This invention did not arise from any funding or sponsorship of the federal government or any other government entity. There was no joint research agreement of any kind that contributed in any way to this invention.

BACKGROUND OF THE INVENTION

1. Technical Field

This invention relates to testing and qualification of panel products and more specifically to the panel products destined to be used under shear stress such as wood I-joist web members or similar applications in which the shear strength of the panel materials is an important design parameter.

2. Importance of the Invention and Prior Art

Particleboard panel products are manufactured by producing a flow of wood pieces of varying dimension ranging in size from wood dust to large flakes or strands, mixing with a resin-wax binding agent and followed by forming a mat of the wood particle—resin—wax mix and placing the mat in a press where the resin is cured under heat and pressure thereby binding the particles together and forming a useful panel product. A wide variation in wood particle type and resin content is used and therefore a wide variation in physical properties of the panel products is available for various applications. When such a panel is to be used for a structural application it is essential that the characteristics of the wood particles, resin, wax and pressing time and temperature be controlled so that the desired properties emerge in the finished goods. For enhanced properties the wood is prepared in strands cut along the grain direction of the wood, and the strands are oriented in a preferred direction in the process of forming the mat before it goes into the press.

Plywood may be manufactured using a wide variety of wood veneer species and grades, and varying in the number of plies, thickness of the wood veneer, as well as resin and pressing time and temperature. If plywood is to be used in a shear loading configuration it is important to know the shear strength in plywood.

For the manufacturer of the wood I joist product, web material may be purchased from a variety of sources and it is essential to the integrity of the I-joist product that the panel products meet requirements for durability, thickness and shear strength. Because the wood I-joist is replacing the wide solid-sawn wood joist in much residential and light commercial construction, it is important to public safety that these materials be properly tested in an on-going quality control program.

ASTM D5055 "Standard Specification for Establishing and Monitoring Structural Capacities of Prefabricated Wood I-Joists" refers to ASTM D1037 in respect of shear strength in the web members of the composite wood I-joist. Therefore the need is established for an accurate testing machine that will perform the required testing. With increasing volume of these products going into construction, a test that requires a minimum of labor input is also very desirable.

With panel products manufactured as plywood or particleboard being used more extensively as web members in a wood "I" joist configuration it is imperative that the horizontal shear strength of these panel products be verified and properly characterized so that the design of these wood I-joist products will perform as bending members in structural service.

DEFINITIONS

"Guard door"—An operator safety door that prevents access to moving parts while the equipment is in motion.

"Testing rails"—Part of a prior art "rail testing" apparatus which capture a rectangular panel specimen for performing a shear test in a universal testing machine.

"Roller rails"—In the present invention the roller rails provide a working surface upon which cam rollers ride to carry the weight of a clamp assembly.

"Unclamped area"—That portion of a panel specimen which is outside the grip area of an upper clamp means and a lower clamp means.

BRIEF SUMMARY OF THE INVENTION

The present invention is a tester for performing edgewise shear tests on samples of panel product in which three loading configurations are provided to simulate prior art diagonal loading with or without rotational constraint, and a third configuration to simulate the shear stresses that exist in a structural assemblage including panel or sheet goods in which such goods are used as a web member in a beam configuration as a box beam or an "I" beam and knowledge of the shear strength is essential for producing a safe structure. The present apparatus operates under computer-control to automatically perform the shear test and record the test results

BRIEF DESCRIPTION OF THE DRAWINGS

The present invention is presented in a preferred embodiment in the following drawings.

FIG. 17 is a prior art apparatus with specimen under load in a conventional test machine.

FIG. 18 is an edge-view of a prior art specimen under load in a conventional test machine.

DETAILED DESCRIPTION OF THE INVENTION

Figure 1:
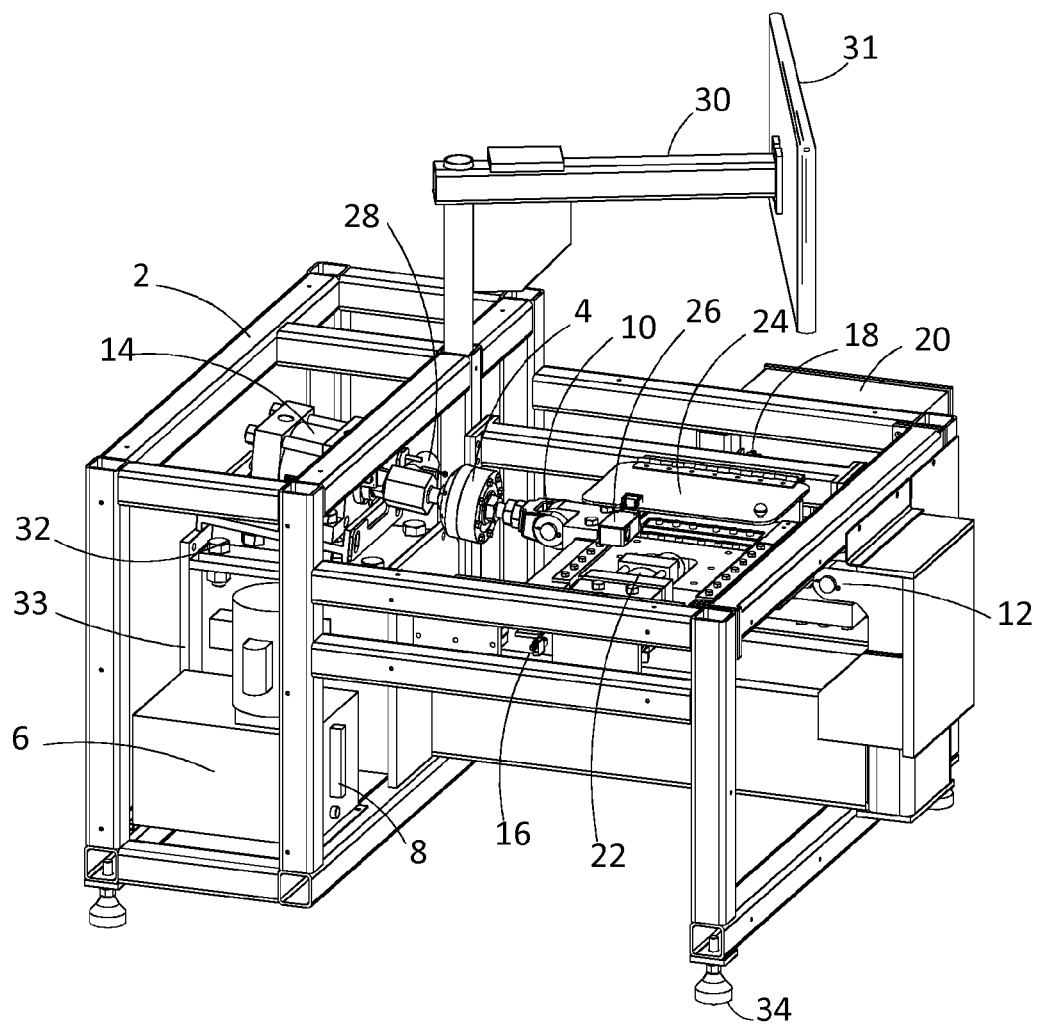
FIG. 1 is an isometric view of the Apparatus with covers removed to show internal components.

FIG. 1 shows the present apparatus in an isometric view. A framework 2 encloses a hydraulic pump 6 with tank sight gauge and thermometer 8, a load cylinder 14, a displacement sensor 28, a load cell 4 a clevis eye connection 10 a guard door lock 26 a guard door 24, a photo sensor transmitter 16, a photo sensor receiver 18, an upper clamp assembly 22, and a lower clamp not shown with a pivot means 12, an electrical control cabinet 20, a panel-type touch-screen PC computer 31 and mounting means 30 and resting on adjustable feet 34. The present apparatus is shown in FIG. 1 arranged to perform a rail shear test according to ASTM D 1037 Sec 130 with full conformance with the loading arrangement in which the edgewise specimen is loaded along a diagonal direction.

The load cylinder 14 mounting arrangement includes an angled bracket 32 that establishes the loading angle in the specimen. An alternative loading arrangement of horizontal shear through the horizontal centerline of the specimen is achieved by removing angled bracket 32, changing clevis eye connection 10 for a new part not shown, and replacing angled roller rails 11, 13 and 15 shown in FIG. 4 for the upper clamp assembly with non-angled roller rails. The lower clamp assembly is then locked in place for operation in horizontal shear mode.

Figure 2:
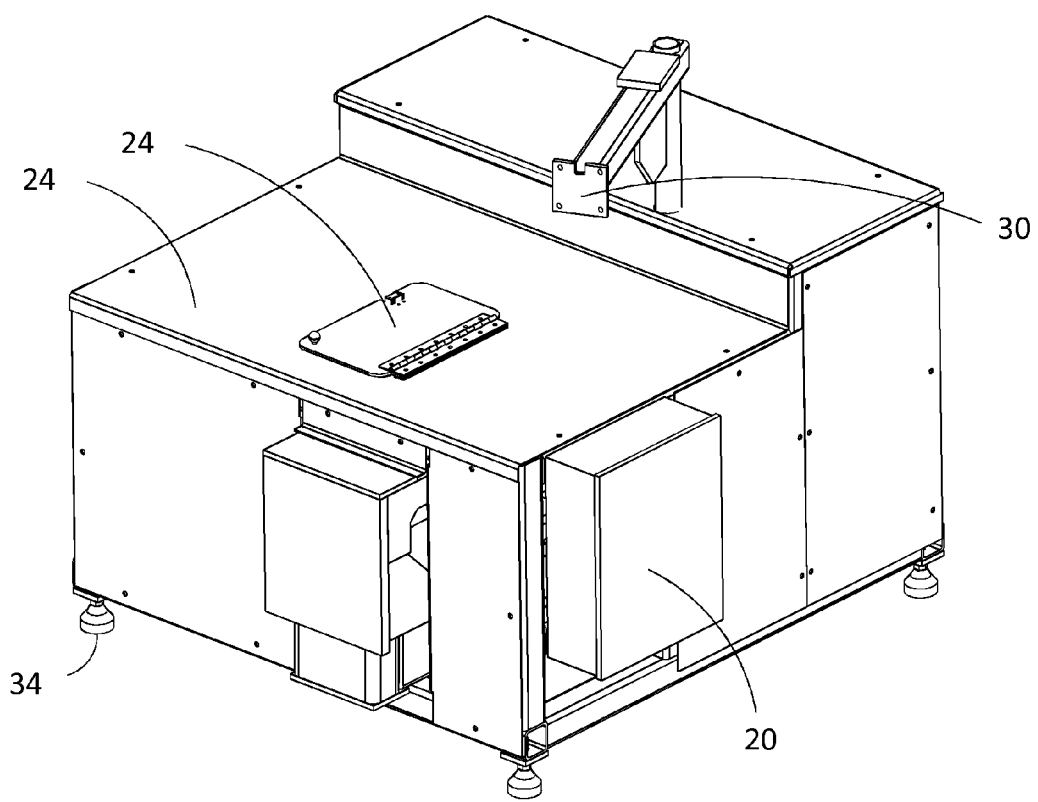
FIG. 2 is an isometric view of the Apparatus with covers installed showing location of major components.

FIG. 2 shows the apparatus of the present invention with safety covers in place. The guard door 24 is unlocked only when the hydraulic system is disabled and the clamp cylinders and the load cylinder cannot move. Computer mounting arm 30 can pivot about its mount in the frame for convenient location of the computer screen not shown. Electrical power is connected to the electrical control enclosure 20 and the machine rests on adjustable mounts 34 for leveling the machine and allowing for uneven floor surface.

Figure 3:
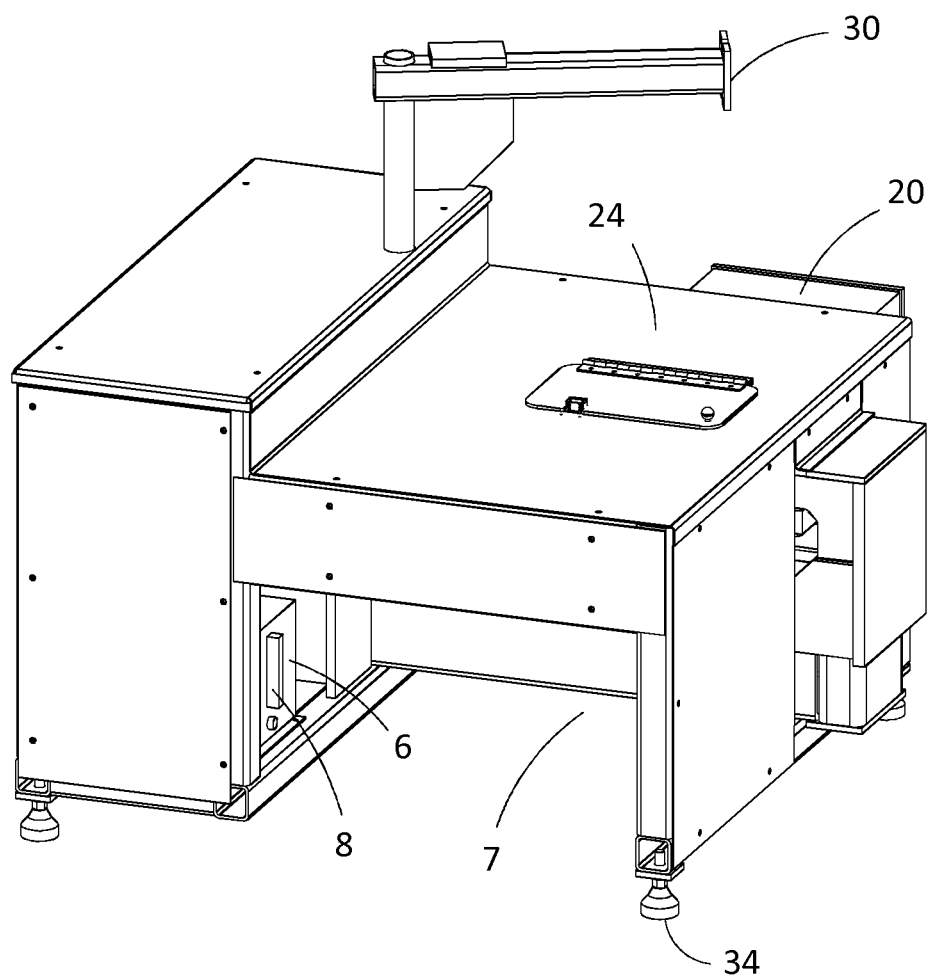
FIG. 3 is an isometric view of the Apparatus with covers installed showing location of hydraulic pump, tank fill gauge and thermometer.

FIG. 3 shows a view of the present apparatus in which an opening 7 is provided for inserting a bin for catching tested specimens when they drop out of the machine after test. The hydraulic pump 6 and sight gauge for oil tank 8 are located in view of an operator for convenient checking.

Figure 4:
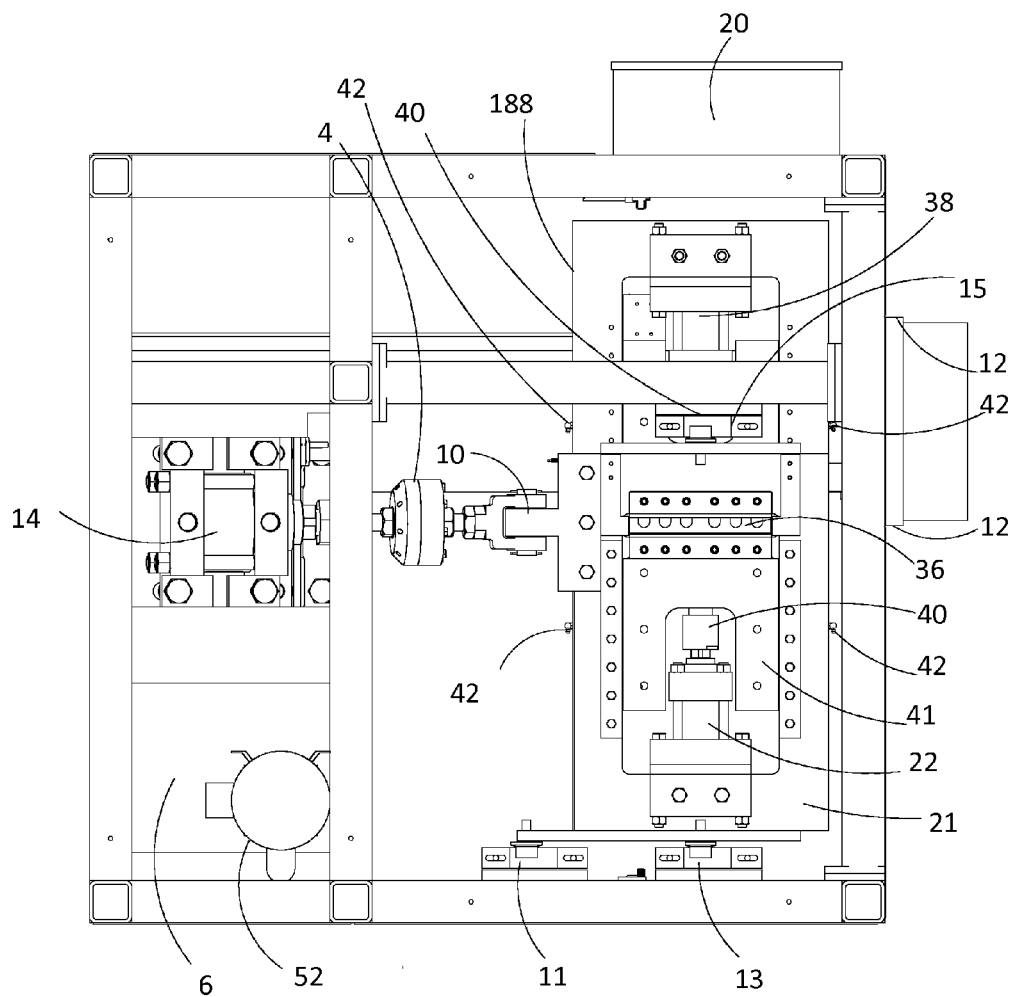
FIG. 4 is a top view of the Apparatus showing the arrangement of clamps and loading cylinder.

The top view of the present apparatus in FIG. 4 shows the location of hydraulic pump assembly 6, loading cylinder 14, load cell 4, clevis connection 10, and replaceable angled roller rails 11, 13 and 15 which carry the weight of the upper clamp assembly 21 including clamp cylinder 22 coupling device 40, clamp slide 41 and lubrication connections 42. A lower clamp assembly 188 is suspended on a distal side by pivot pins, 12 and on a proximal side by pneumatic cylinder means 190 shown in FIG. 12. Lower clamp assembly 188 includes a clamp cylinder 38. In operation a specimen is placed in opening 36 shown in FIG. 4 where it is held in place by pneumatic gate means 166 shown in FIG. 12. Hydraulic closure of clamp assemblies 21 and 188 shown in FIG. 4 is followed by load applied by load cylinder 14 while testing force is measured by load cell 4 and displacement is monitored by displacement sensor 28 (shown in FIG. 1.)

Figure 5:
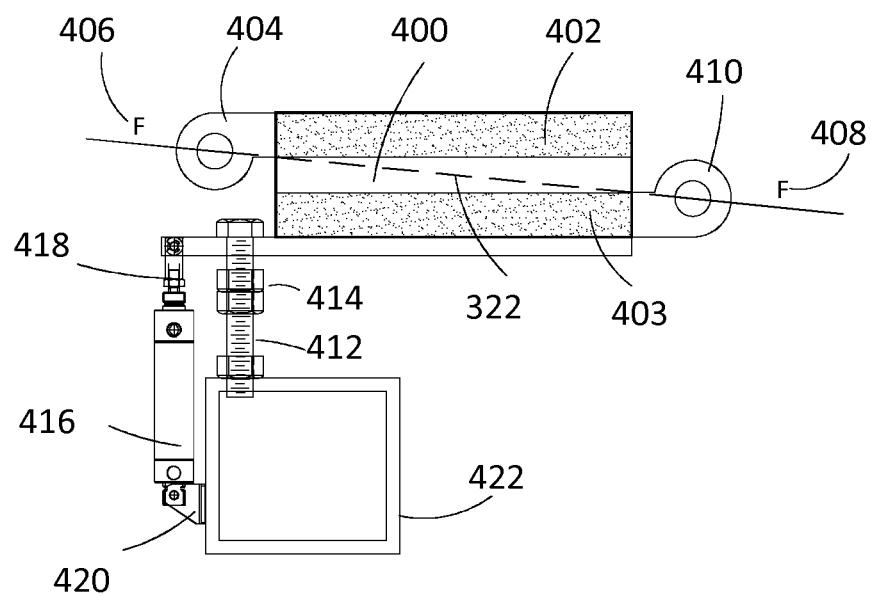
FIG. 5 is a mechanical schematic describing the loading arrangement for shear testing in the present invention in a first and second loading configuration.

FIG. 5 is a mechanical schematic showing the specimen 400 captured by grips 402 and 403 with shear force 406 and 408 being delivered through pivot connections 404 and 410. Pivot 410 is attached to beam 422 by means (not shown), and shear force 406 is delivered such that the line of force through the specimen 322 is in a diagonal direction through the specimen from corner-to-corner of the unclamped area. The weight of the lower grip assembly 403 is supported by pneumatic lift cylinder 416 coupled by pivot means 418 to the lower clamp assembly. Pneumatic lift cylinder 416 is attached to support beam 422 by pivot mount 420. Stop bolt 412 is attached to support beam 422 and jam nuts 414 are placed allowing the lower clamp mechanism to rotate between limits established by the head of stop bolt 412 and the location of jam nuts 414 so that displacement of the specimen arising from shear deflection will allow the lower clamp 403 to pivot about its mounting pivot 410 thereby displacing pneumatic lift cylinder 416.

A second loading method places lower clamping means 403 in a fixed position by adjusting jam nuts 414 to prevent the lower clamping means from pivoting, thereby holding it in a fixed position.

Figure 6:
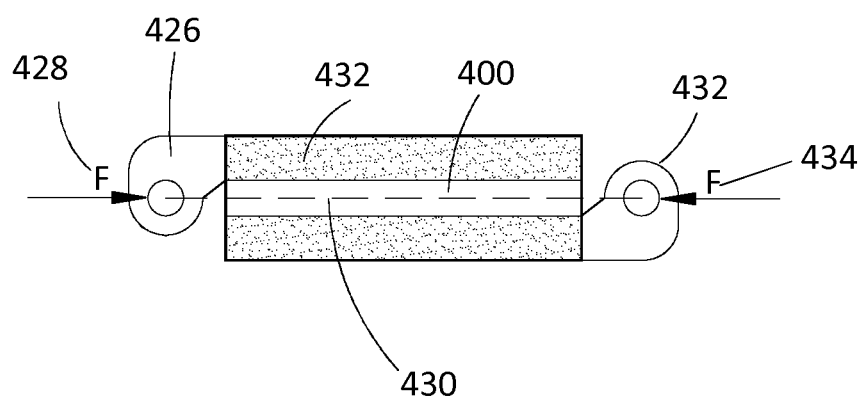
FIG. 6 is a mechanical schematic describing the loading arrangement for shear testing in the present invention in a third loading configuration.

In an alternative loading arrangement shown in FIG. 6 the line of force 430 is directed along the centerline of the specimen by the present invention apparatus by making some simple adjustments to the apparatus whereby the shear force 428, 434 is directed through a pivot point 426 and 432 the centerline of which coincides with the centerline of the specimen 400. This mode of operation is enabled by removing the load cylinder angled bracket 32 shown in FIG. 1, and mounting the load cylinder directly to the support frame 33, also shown in FIG. 1 replacing angled roller rails 11, 13 and 15 shown in FIG. 4 are removed and replaced with non-angled roller rails. Thus an important feature of the present invention is its adjustability to 3 different loading arrangements.

Figure 7:
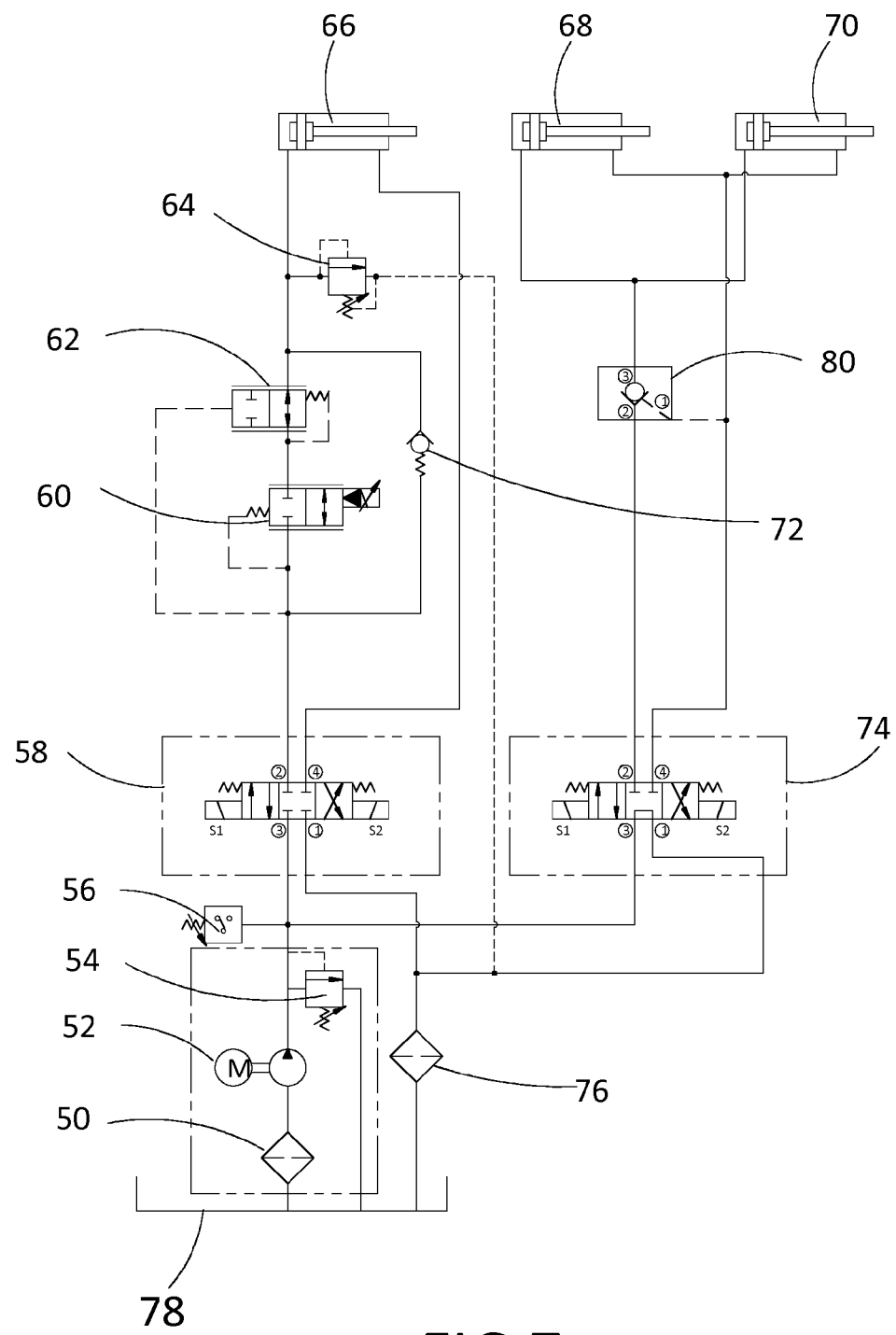
FIG. 7 is a hydraulic schematic showing pump, controls, and cylinders.
Figure 12:
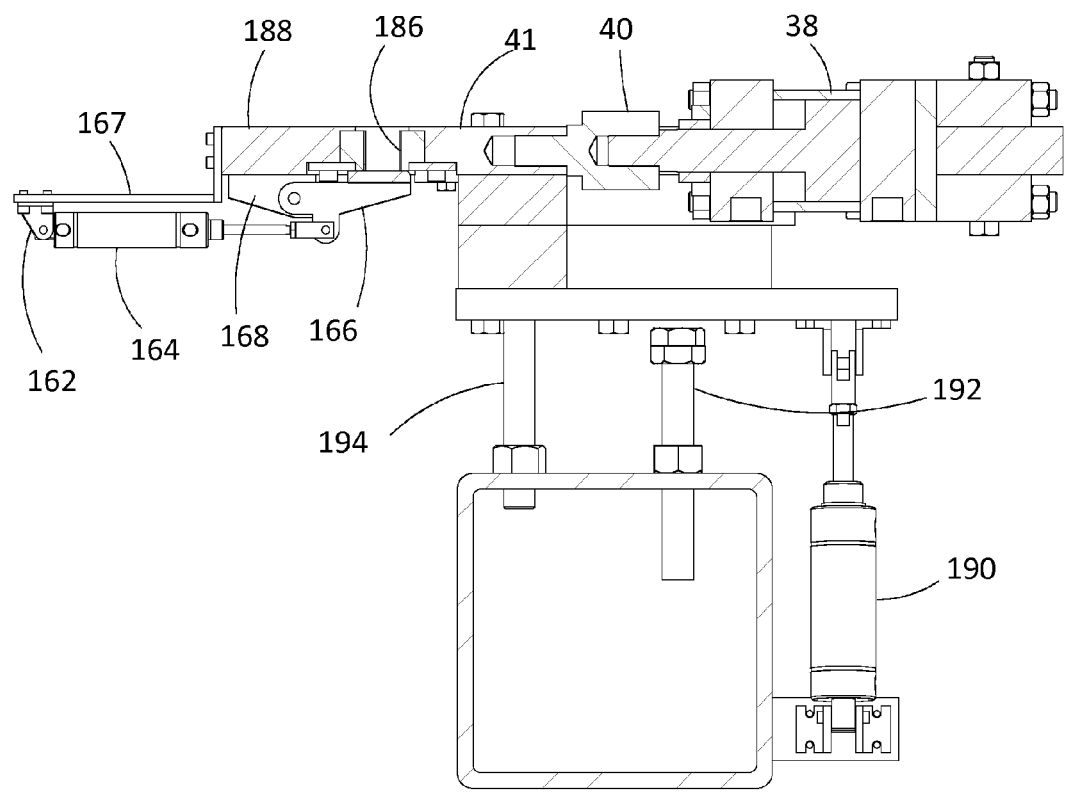
FIG. 12 is a vertical cross section of a lower clamp showing pneumatic gate, pneumatic lift cylinder and travel stops for lower clamp assembly.

FIG. 7 shows the hydraulic schematic diagram, including reservoir 78 from which oil is drawn through input screen 50 by pump 52 and delivered to clamp valve 74 and hydraulic shear valve 58. With the clamp cylinders 68 and 70 (schematic representation of clamp cylinders 22 and 38 respectively in FIG. 4) activated and closed as indicated by pressure switch 56; the load cylinder 66 (a schematic representation of load cylinder 14 on FIG. 1 and FIG. 4) is then activated by valve 58. A proportional control valve 60 with check valve 72 and pilot bypass valve 62 operate to deliver a controlled flow of hydraulic oil to load cylinder 66 until failure of the specimen which is indicated by a reduction of force in load cell 4 (FIG. 1). Proportional control valve 60 is electrically driven by means of a pulse-width modulated control voltage whereby the flow rate of hydraulic fluid is adjustable under computer control. The maximum pressure delivered to load cylinder 66 is limited by adjustable bypass pressure relief valve 64. Upon failure of the specimen, gate 166 shown in FIG. 12 is opened, the clamp cylinders 68 and 70 are retracted, and finally the load cylinder 66 is retracted. Upon full retraction of all the cylinders, the pump is turned off and the guard door lock 26 in FIG. 1 is deactivated.

Figure 8:
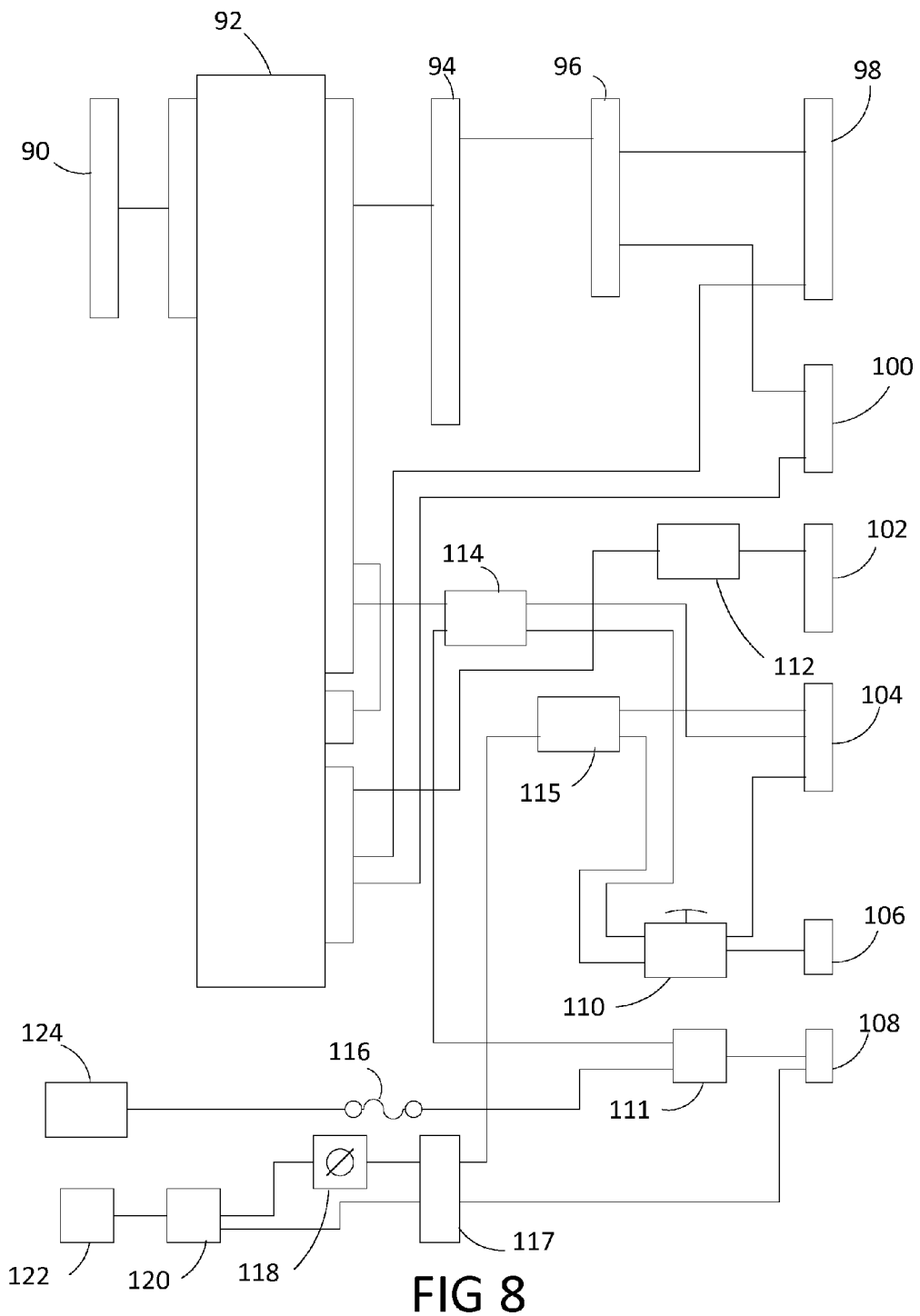
FIG. 8 is an electrical connection diagram showing components inside the electrical control cabinet.

The control cabinet 20 in FIG. 1 and FIG. 2 contains the electrical apparatus shown in FIG. 8. This includes an Ethernet connection 90; a processor 92, relays 94 and 96, input power connections 122 and 124, power switch 118, terminal blocks 117, fuse 116, Rino PSB24-240 power supply 115, a Leuze RL-11 safety switch 114, load cell amplifier 112, and safety lockout switch 110 and connection 106 to guard door lock. In one preferred embodiment of the present invention the processor 92 is a Galil RIO-47112 processor card. Hydraulic valve control connector 98, gate control connector 100, load cell connector 102, external safety lockout switch connector 104 and hydraulic pump motor connections 108 are included in the control cabinet.

Figure 9:
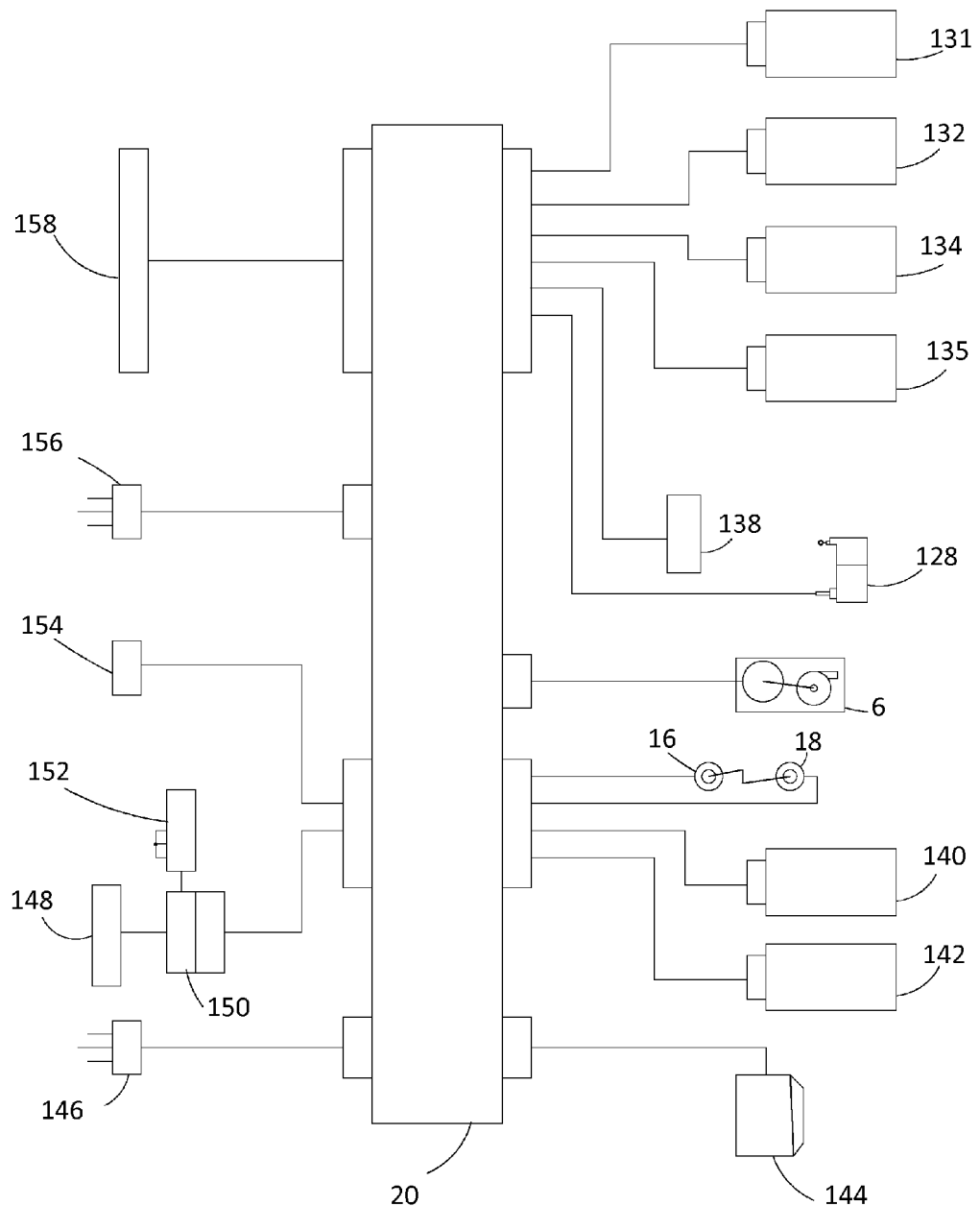
FIG. 9 is an electrical connection diagram showing components outside control cabinet.

Electrical connections external to the electronics enclosure 20 in the apparatus of the present invention shown in FIG. 9 include electrical power connections 146 and 156, an external moveable lockout safety switch 154, guard door lock 148 with its connector 150, and a dummy plug 152 that can be used to deactivate the guard door lock when the top cover is removed for calibration activities. Connection 132 provides switched electrical power for pump 52. The guard door is locked by means of an electrically activated lock 148, a Leuze MLM24, which prevents the apparatus from operating with guard door open, and prevents the guard door from being opened while the apparatus is in motion. A connection 128 to a displacement sensor 28 shown in FIG. 1 for measuring the motion of the top clamp assembly is shown on FIG. 9. Also included are connection 131 to hydraulic shear valve 58 in FIG. 7, connection 134 to hydraulic clamp valve 74 in FIG. 7 and connection 138 to hydraulic proportional control valve 60 in FIG. 7, connection 135 to pressure switch 56 in FIG. 7, connections to photo sensor transmitter 16 and receiver 18, connection 140 to pneumatic gate air valve 216 in FIG. 14, connection 142 to pneumatic lift cylinder valve 212 in FIG. 14, and connection 144 to load cell in FIG. 1 and FIG. 4.

Figure 10:
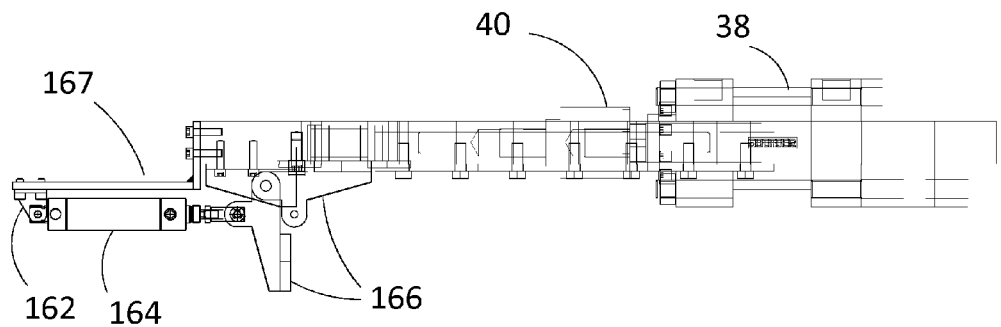
FIG. 10 is a vertical side view of a lower clamp including a pneumatic gate.

FIG. 10 shows an elevation view of the lower clamp assembly including a pneumatic gate 166 which is activated by a pneumatic cylinder 164. The pneumatic cylinder 164 is mounted to bracket 167 by means of pivot brackets 162. Hydraulic cylinder 38 activates the clamp mechanism through coupler device 40 which allows for radial misalignment and prevents binding in the assembly.

Figure 11:
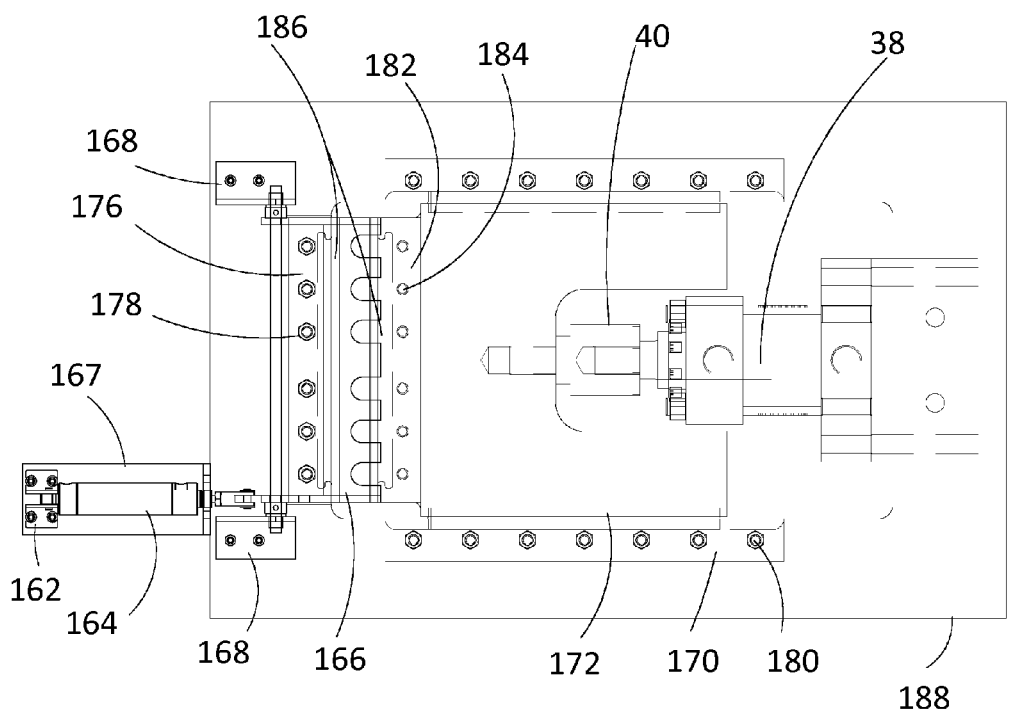
FIG. 11 is a bottom view of a lower clamp showing arrangement of hydraulic cylinder, coupler, slider, jaws and pneumatic gate.

FIG. 11 shows lower clamp assembly 188 with cylinder 38, coupling device 40 provide clamping force to the specimen under test. Bearings 172 are captured by bearing retainer 170 which bearing retainers are secured by cap screws 180. Pneumatic gate 166 pivots about bearings mounted in brackets 168. Removable jaw grips 186 are held in place by plates 176 and secured by screws 178. When the pneumatic gate 166 is in its closed position (cylinder 164 extended), the gate is flush against the bottom of the grip surfaces 186, and the notches in gate 166 clear the mounting screws 184 allowing the clamp to open or close with the gate in its cylinder-extended position. After the testing is complete on a specimen the clamp jaws are opened, the gate is opened and the loading cylinder 14 (in FIG. 1) is retracted. These actions will normally dislodge a specimen that may be stuck to the clamp jaws. The arrangement of gate and clamp grip pieces of the present invention provides for very accurate positioning of a specimen when it is simply dropped into the clamp jaws.

The cross sectional drawing of FIG. 12 shows the lower clamp assembly 188 in vertical cross section with suspension system rotated 90 degrees about a vertical axis. Features of the lower clamp including clamp cylinder 38, coupling means 40, grip surface 186 and gate 166 with its actuating air cylinder 164, cylinder pivot mount 162 and mounting bracket 167 are visible along with the lift means actuator and motion limit means. In this embodiment the travel stop bolt 192 is separate from the travel limit stop bolt 194. It is noted that the function of cylinder 190 may be replaced by a compression spring means or air bag means to perform the same function in operation of the apparatus.

Figure 13:
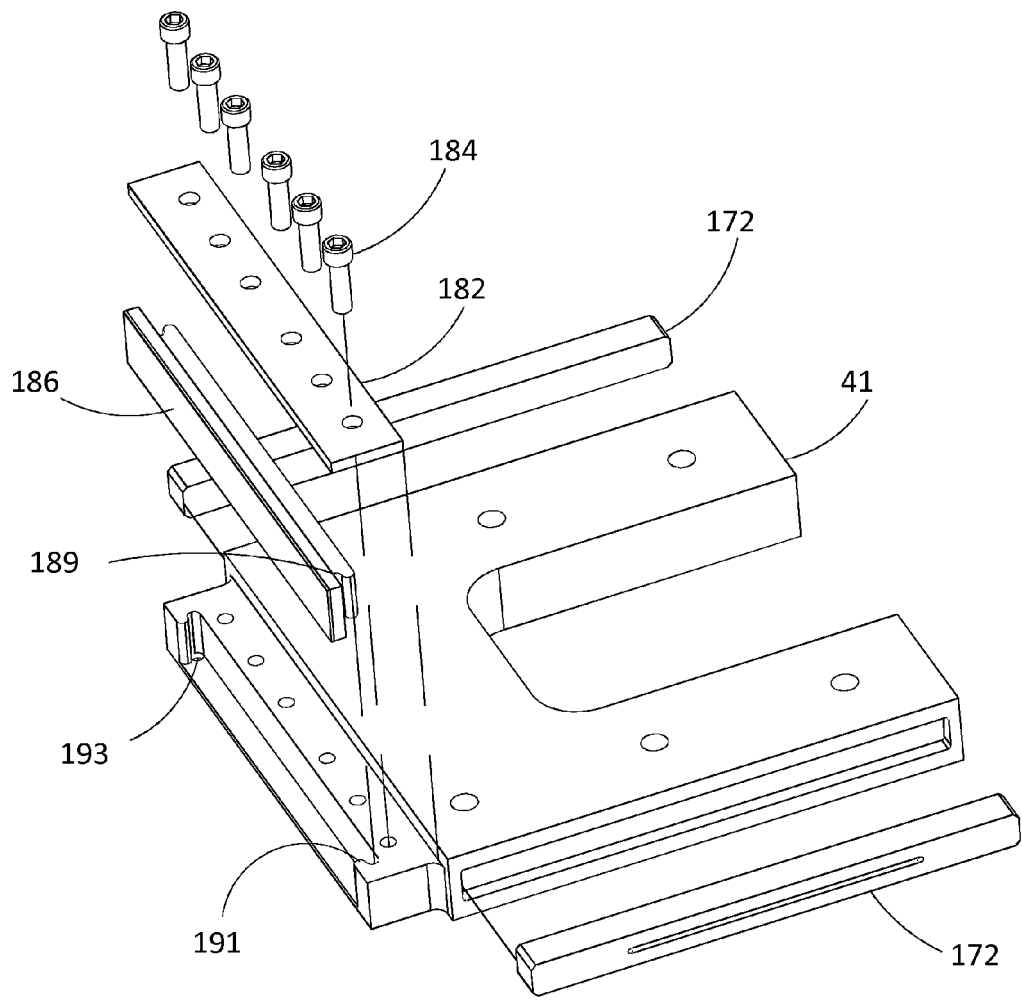
FIG. 13 is an isometric view of clamp slider showing slide bearings, jaw insert and jaw retaining means.

FIG. 13 is an exploded view of the sliding part of clamp assembly 188 with bronze bearing members 172 fitting in machined pockets on opposite sides of clamp slide 41, and end 189 of removable grip 186 fitting into matching receptacle 191 with projection 189 providing a capture of removable grip 186. Access holes 193 at the two corners of clamp slide 41 are provided in case of difficulty in removing grip 186 so that a drift punch may be used as a persuading influence. Grip 186 is captured by its ends and with a retainer plate 182 held in place by screws 184. The grip surface of 186 is roughened by means of a metal spraying process that leaves a rough sandpaper-like finish of hard metal welded to the treated part. Identical grip parts 186 are used for both faces of upper and lower clamp assemblies.

Figure 14:
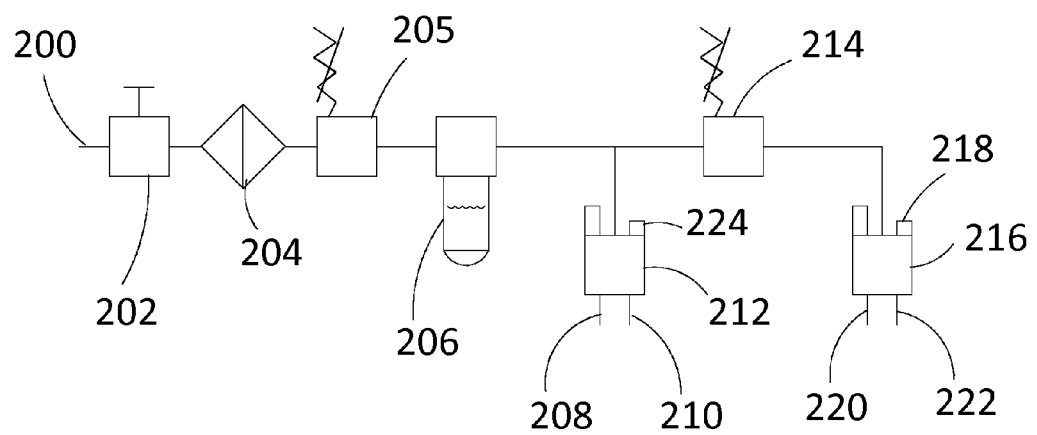
FIG. 14 is a pneumatic schematic diagram showing input connection, valve, filter, lubricator and valves.

The pneumatic controls shown in FIG. 14 include an attachment 200 for an air hose, a stop/waste shutoff valve 202 which in the preferred embodiment also has a lock-out capability. In line are filter 204, regulator 205, lubricator 206, and pneumatic 4-way valves 212 and 216 for the lift and gate cylinders respectively. Connections 208 and 210 attach to pneumatic lift cylinder 416 in FIG. 5 or 190 in FIG. 12. The gate cylinder can be operated at a lower pressure, so pressure regulator 214 reduces the air pressure to valve 216 which is attached to the gate cylinder by connections 220 and 222. Mufflers 218 and 224 provide a more pleasant environment for the work force which may be operating in the vicinity.

The pneumatic lift cylinder 190 of FIG. 12 may be alternatively connected to the output of the lubricator 206 because operation of the apparatus does not require that pneumatic lift cylinder 416 be deactivated thereby eliminating the need for valve 212.

Figure 15:
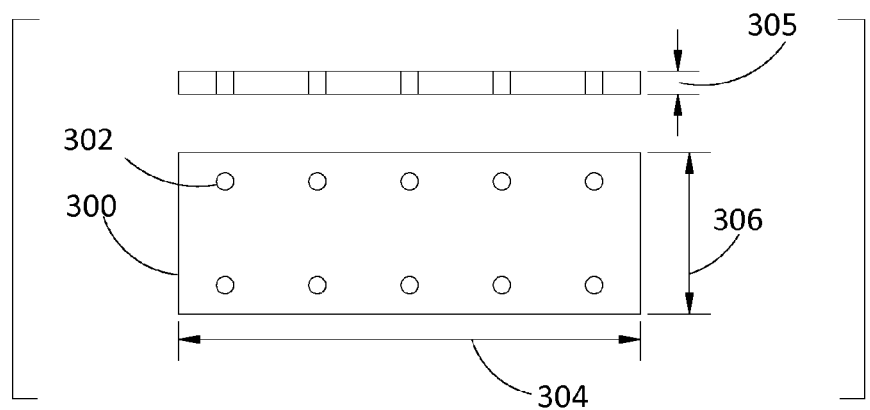
FIG. 15 is a prior art specimen showing preparation for connection to testing rails for testing in a conventional universal test machine.

FIG. 15 shows a prior art specimen prepared according to ASTM D1037 for testing by means of prior-art rail shear fixtures in a conventional universal test machine. In addition to cutting the specimen 300 to size with length 304, thickness 305 and width 306, holes 302 must be drilled in the specimen with care taken to make clean, accurate holes, which can be a challenge with some particleboard materials.

Figure 16:
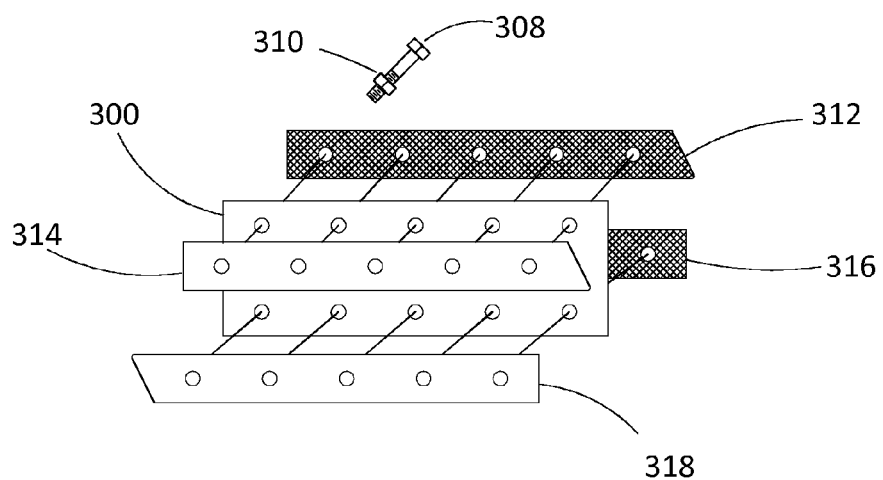
FIG. 16 is a prior art fixture connection to a test specimen using bolts.

FIG. 16 shows the arrangement of rail shear fixture pieces 312, 314, 316 and 318 attached with bolts 308 and nuts 310 through all the matching holes. The fixtures have a machined grip surface on the contact side, and all the bolts must be tightened to prevent slipping under test load. Test results may vary with bolt tension, a factor that is eliminated with the controlled clamping pressure of the present invention.

FIG. 17 shows a side view of the specimen when placed in a universal test machine and placed under load. Once the specimen is prepared and fastened in the test fixtures, a load 320 is applied so the line of shear force 322 is diagonal from corner-to-corner of the unclamped area of specimen 300. Bolts 308 hold the testing rails 314 in place.

FIG. 18 shows an edge view of the specimen 300 when rail shear fixtures are attached and the specimen is placed under load. This view illustrates the position of bolts 308, nuts 310, and testing rails 314 and 318 with the specimen under load force 320.

Figure 19:
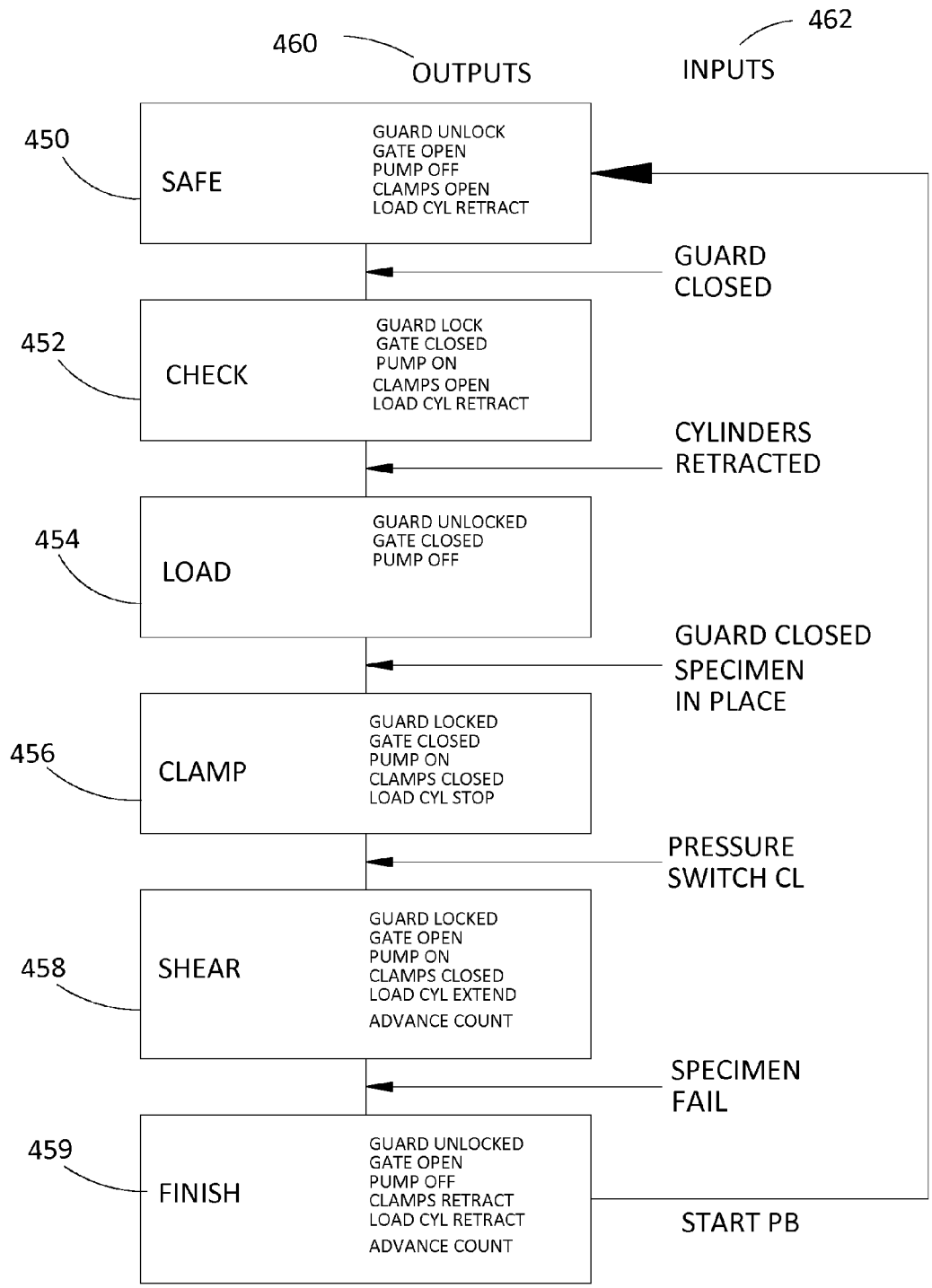
FIG. 19 is a state diagram for the control functions of the present invention.

FIG. 19 illustrates the operating sequence for the present invention. The control function can be illustrated as a state machine that goes through a series of states or stages in the testing sequence. In the first operating state 450, the control outputs unlock the guard door 24, open the gate 166, the hydraulic pump 6 is OFF and clamp cylinders 22 and 38 and load cylinder 14 are retracted.

Figure 20:
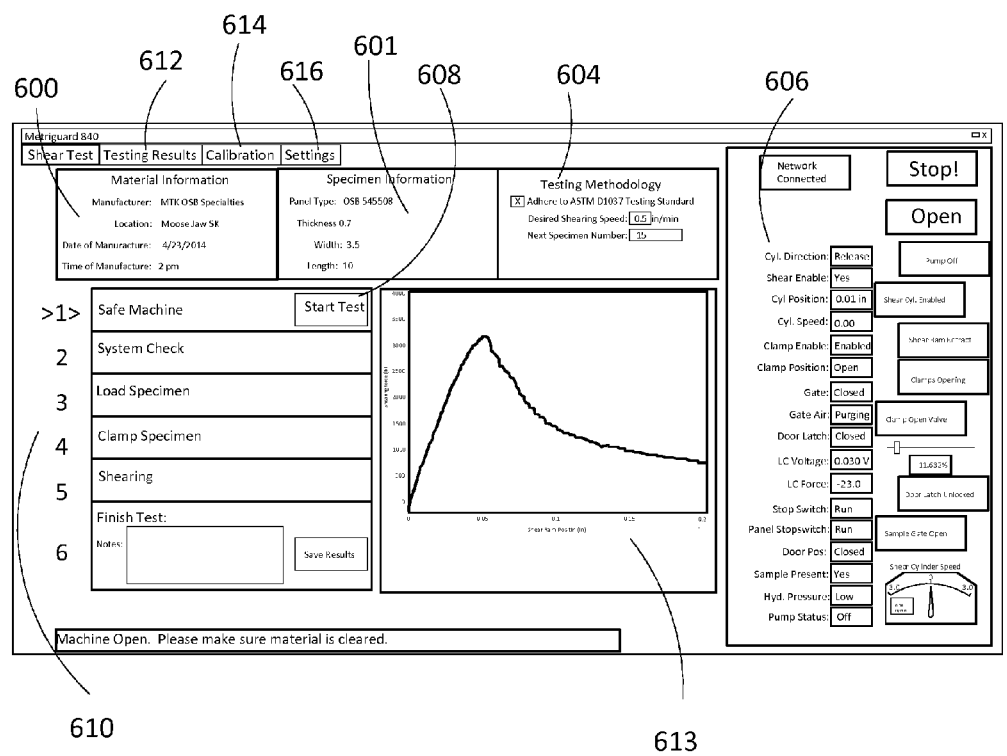
FIG. 20 is a diagram of a computer control screen showing specimen data entry, testing methodology settings, control panel for controlling individual functions, and a state screen where operator inputs are entered to start the test sequence and save test results.

When the "start test" button 608 in FIG. 20 is activated and the guard door 24 is closed there is a brief activation of the hydraulics to assure cylinders 22, 38 and 14 are retracted and gate 166 is closed in the Check state 452. Upon completion of this stage the LOAD state 454 is entered the guard door 24 is unlocked and a specimen may be placed in the apparatus.

When the specimen is in place and the guard door 24 is closed the clamp state 456 is entered. The guard door 24 is locked, the pump 6 is started and the clamp cylinders 22 and 38 are activated. When the hydraulic pressure reaches its preset point on pressures switch 56, the SHEAR state 458 is entered. During this state the guard door 24 remains locked and the load cylinder 14 is activated while the load cell 4 measures force and the displacement of the specimen is recorded therewith. Upon failure of the specimen as indicated by the measured force reaching a preferred fraction of the measured peak force, and deflection in the specimen reaching a preferred distance the test is terminated and guard door 24 remains locked, the gate 166 is opened, the clamp cylinders 22 and 38 are retracted and the load cylinder 14 is retracted. Upon completion of these actions, the state is switched to FINISH 459 at which point the operator may enter notes for the record associated with the individual specimen and save the test results. The specimen count is advanced and the test results may be saved or discarded by selection of the operator.

These operating states are illustrated on the control screen display shown in FIG. 20. On this panel material information 600 is entered along with specimen information 601 and testing methodology 604. Direct control of the various machine functions is available on the control panel 606. For a normal test the material information, specimen information and testing methodology are entered. Then the "Start Test" button 608 is activated in the state sequence panel 610. With the guard door 24 closed, the apparatus goes through the testing stages enumerated above to complete the shear testing of a specimen. Graphical display 613 shows a plot of load force as a function of shear strain or displacement.

In addition to the Shear Test screen, the operator may select to view Testing Results 612, open a Calibration 614 screen or a Settings 616 screen to adjust machine settings.

In the Calibration 614 screen the top cover 25 (in FIG. 2 and FIG. 3) of the machine is removed, a dummy plug is inserted in place of the cable leading to the guard door lock 26; the load cylinder clevis attachment 10 in FIG. 4 is removed and replaced with an independent load cell with a load button attachment to the upper clamp assembly 21. An aluminum block (not shown) is placed in the specimen location, and with the load pressure relief valve 64 of FIG. 7 adjusted to a minimum setting the pump is activated to clamp the dummy specimen and apply load to the load cell 4. Simultaneous readings are captured in the machine electronics and on the independent load cell readout at a preferred number of load settings established by adjusting the load pressure relief valve 64 on FIG. 7. These reading pairs are used to adjust internal processing to establish a 1:1 correspondence between machine load readings and independent load cell readings.

The independent load cell and its associated readout act as a secondary standard, and must have their calibration checked on a periodic basis according to rules established by an independent calibration agency.

Control Software

The control software for the apparatus of the present invention consists of a graphical interface designed to run on Microsoft Windows 7 or 8. The program is implemented using C# and the Microsoft WPF/.NET platform. The hardware is controlled by sending messages via Ethernet to a Galil controller (92 of FIG. 8).

Data storage for test results is managed using a MySQL database and consists of two tables: a specimens table to store the results of each specimen, and a "LoadCellData" table to store the raw load cell readings for each specimen.

The control architecture of the program includes a scripting language for implementing complex control sequences. The scripting language interpreter manages background processing and a halting mechanism to ensure that complex operations can be safely discontinued and the machine brought to a safe state at any time.

Features and Advantages of the Present Invention and Comparison with the Prior Art The prior art test fixture shown in FIG. 17 and FIG. 18 was devised many years ago which consisted of a 4-piece rail arrangement including a roughened grip surface facing the specimen, and bolted to the panel specimen, then the panel specimen with rail grips was placed in a universal testing machine, load applied to the opposite ends of the rail fixture to induce a shear stress in the specimen along a diagonal direction. The shear strength was then reckoned as the force divided by the (product of thickness and length), i.e., the cross sectional area in the shear plane of the specimen is slightly larger than the shear plane area used in the calculation. The strength is reported as the force per unit area reckoned as the thickness times the specimen length. Whether the discrepancy in the calculation is significant remains to be determined.

Specimen preparation for the prior art apparatus involves first cutting a panel into specimens for test, drilling holes in the specimen through which clamping bolts may pass, bolting the testing rails to the specimen and then carrying out the test in a calibrated loading device in which the load is measured and the rate of movement is controlled. This is a tedious process of cutting, drilling, bolting and testing that is required to achieve a measurement of shear strength in a specimen.

One shortcoming of this test method is that the shear stress is applied in a diagonal direction in the specimen, whereas in the wood I joist the stress is purely in the long direction of the web member, so there may be a mischaracterization of the strength in this regard.

This shortcoming is removed in the present apparatus by using the horizontal shear option in testing. In this case the failure stress is calculated correctly on the basis of the cross section area of thickness times specimen length, whereas in the diagonal stress case the actual stressed area is larger than the area used in the calculation, leading to a possibly larger calculated failure stress than actually experienced by the specimen. It remains to be seen whether this is a significant factor in the error budget of this important test.

Another shortcoming in the prior art method is the requirement for extra specimen preparation in drilling holes and bolting the testing rails to the specimen. This shortcoming is removed by hydraulic actuated clamping which eliminates the need for drilling and bolting the test specimen.

A prior art apparatus provided hydraulic clamping but provides only fixed second clamping means, so the stresses in the specimen are not properly simulating those found in the conventional rail shear apparatus and said prior art apparatus was not capable of placing the shear stress along the horizontal centerline of the specimen. The present apparatus avoids this issue by providing a second pivot point for a second lower clamp assembly that is in line with the diagonal shear stress such that the apparatus can properly simulate the stresses applied in the conventional bolted rail shear means.

These fundamental features together with a computer numerical control system for operating the hydraulic controls and data collection provide a complete testing process that is operated by simply opening a guard door, dropping the specimen in place, closing the door and activating the system. From that point forward, the apparatus clamps the specimen, applies the shear test load and records the force and deflection until the specimen fails, stores the test data, opens the clamps, opens a pneumatic gate and retracts the loading cylinder, and allow the specimen to fall into a discard bin. The loading rate is under computer control, and the guard door is locked during the test to prevent injury to the operator while the test is in progress.

The present invention apparatus operates under computer control whereby the control functions are driven by computer software and data collection is performed on a continuous basis while load is applied so that both stress and strain are recorded, and failure stress (force per unit area) is calculated and recorded for each specimen. The present apparatus automatically records the data for each specimen in a computer database file which eliminates human recording errors and reduces consumption of paper and pencils thereby having a positive influence on the environment.

Operator safety is an important feature of this invention. Hand operation of bolt tightening means is eliminated. This means that grip pressure is controlled and adjustable. The apparatus is fully enclosed and a guard door is locked while moving parts are in motion to prevent stray fingers or other appendages from interfering with the proper operation of the apparatus as well as incidentally preventing traffic accidents while pinch victims are raced to the nearest medical facility for reattachment treatments.

One other prior art apparatus has been developed which embodies only one of the three loading configurations of the present invention and none of the safety features. The inventors are not aware at the time of filing of any publications in respect of this prior art apparatus.

The exemplary embodiments shown in the figures and described above illustrate but do not limit the invention. In compliance with the statute, the invention has been described in language more or less specific as to structural features. It is to be understood, however, that the invention is not limited to the specified features shown, because the means and construction herein disclosed comprise a preferred form of putting the invention into effect. The invention is, therefore, claimed in any of its forms or modifications within the proper scope of the appended claims appropriately interpreted in accordance with the doctrine of equivalents.

The invention claimed is:

1. A testing apparatus for measuring a shear strength of a panel specimen including a first loading configuration and a second loading configuration, said panel specimen having a specimen width, a specimen length and a specimen thickness and having an unclamped area approximately rectangular in shape centrally located in said specimen width and a specimen center located at the middle of said panel specimen width and said specimen length, said apparatus including:
   a. an upper clamp means connected through an upper clamp pivot means, said upper clamp pivot means located on a first preferred loading angle and defining a first rotational degree of freedom about a horizontal axis perpendicular to said first preferred loading angle,
   b. said first preferred loading angle is a preferred diagonal line extending from corner to corner of said unclamped area of said panel specimen and extending outwardly therefrom,
   c. said upper clamp pivot means connected through a load cell to a load cylinder means, said upper clamp means supported by roller means running on angled roller rail means,
   d. Said load cylinder means mounted on a framework means,
   e. said load cylinder means, said load cell, and said angled roller rail means aligned parallel with said first preferred loading angle,
   f. means for measuring a displacement of said upper clamp means,
   g. a lower clamp means connected through a lower clamp pivot means to said framework means, said lower clamp pivot means located on said first preferred loading angle and allowing a second rotation degree of freedom about a horizontal axis perpendicular to said first preferred loading angle,
   h. a lower clamp support means including a lift means and a motion limiting means for selectively restraining rotation of said lower clamp means about said lower clamp pivot means,
   i. a control means for controlling a testing process, said testing apparatus providing selectable loading configurations whereby a shear force is applied along said first preferred loading angle with a first loading configuration with said second rotational degree of freedom in said lower clamp means about said lower clamp pivot means and a second loading configuration in which said motion limiting means prevents rotation about said lower clamp pivot means whereby said shear strength is determined from a maximum value of said shear force applied at failure of said panel specimen and a cross sectional area of a shear plane.

2. The testing apparatus of claim 1 wherein said lift means is a pneumatic cylinder lift means.

3. The testing apparatus of claim 1 wherein said lift means is a spring lift means.

4. The testing apparatus of claim 1 including a means for capturing and positioning said panel specimen by a pneumatic gate positioned below said lower clamp means whereby said panel specimen may be placed in said upper clamp means and said lower clamp means then upon completion of measuring of said shear strength said pneumatic gate is made to open allowing removal of said panel specimen.

5. The testing apparatus of claim 1 including a third loading configuration wherein said shear force is applied in a second preferred loading angle extending through said specimen center in the plane of said panel specimen and parallel with said specimen length.

6. The testing apparatus of claim 5 wherein said load cylinder means is mounted on a removable angled bracket aligning said load cylinder means with said preferred diagonal line and,
   a. removing said angled bracket aligns said load cylinder means with said second preferred loading angle in line with said specimen center,
   b. and said angled roller rails are replaced with non-angled roller rails aligned parallel with second preferred loading angle,
   c. said upper clamp pivot means is relocated on said second preferred loading angle,
   d. said lower clamp means is locked in place by said motion limiting means to prevent rotation about said lower clamp pivot means, whereby a shearing stress is applied parallel with said specimen length and said shear strength is determined from said maximum value of said shear force applied at failure of said panel specimen and the cross sectional area of said shear plane.

7. The testing apparatus of claim 1 wherein said clamp means includes a grip area defined by a grip width and a grip length and said upper clamp means grips said panel specimen over said grip length along said specimen length beginning near a top edge of said panel specimen and extending over said grip width distance along the specimen width direction and said lower clamp means grips said panel specimen over said grip length along said specimen length beginning near a bottom edge of said panel specimen and extending over said grip width distance along the specimen width direction of said panel specimen, said unclamped area comprising the area of said panel specimen unclaimed by said grip area of said upper clamp means and said grip area of said lower clamp means.

8. The testing apparatus of claim 1 wherein said specimen width is approximately 3½ inches, said specimen length is approximately 10 inches and said specimen thickness is in the range of 1/16 inch to 1¼ inch.

9. The testing apparatus of claim 7 wherein said grip width is approximately 1¼ inch and said grip length is approximately 10 inches whereby said unclamped area exposed to shear forces during a test is approximately one inch by approximately 10 inches.

10. The testing apparatus of claim 4 further including controls, hydraulic components, measurement components and pneumatic components enclosed with covers and including an electrical door lock and a safety lockout switch whereby motion of all components is prevented when a guard door is open.

11. The testing apparatus of claim 10 wherein said guard door is locked in a closed position while any internal parts are moving under power.

12. The testing apparatus of claim 11 further including a hydraulic pump, a first electrically activated valve for controlling clamping of said upper clamp means and said lower clamp means, a second electrically activated valve with a proportional flow control valve for controlling position and speed of said load cylinder means, a third electrically activated valve for controlling said lift means whereby motion control of the various components is affected by electrically-activated means.

13. The testing apparatus of claim 12 wherein said control means includes:
   a. locking means for preventing all motion while said guard door is open,
   b. means for adjusting a loading rate,
   c. means for activating a first step in a testing sequence in which a starting condition for the machine is established with said upper clamp means open, said lower clamp means open, said pneumatic gate closed and said load cylinder means retracted to a starting position,
   d. means for activating a second step in said testing sequence with all motion locked out, and said guard door unlocked, and upon insertion of said panel specimen by an operator and closing of said guard door,
   e. means for activating a third step in said testing sequence, locking said guard door, closing said upper clamp means and said lower clamp means,
   f. means for activating a fourth step in said testing sequence, advancing said load cylinder means, measuring said shear force by means of said load cell while measuring continuously said displacement of said upper clamp means,
   g. means for determining a failure of said panel specimen by reduction of said shear force by a predetermined percentage while said load cylinder means continues to advance, and upon said failure of said panel specimen,
   h. means for activating a fifth step in said testing sequence recording test result information including maximum force applied to said panel specimen, recording panel specimen information, load at failure, shear stress at failure and time to failure, opening said pneumatic gate, opening said upper clamp means and said lower clamp means, retracting said load cylinder and unlocking said guard door.

14. The control means of claim 13 wherein said loading rate is controlled by said proportional flow control valve to match a predetermined loading rate.

15. The control means of claim 13 further including processes for calibrating said testing apparatus so that said shear force is reckoned in standard units of force and said shear stress is reckoned in standard units of stress.

16. The control means of claim 13 further including a graphical visual display of said shear force on a first axis and said displacement of said upper clamp means on a second axis.

* * * * *